United States Patent [19]

Martin et al.

[11] Patent Number: 5,130,125
[45] Date of Patent: Jul. 14, 1992

[54] NAIL POLISH TOP COAT

[75] Inventors: Frederick L. Martin, Mesquite; Martin V. Onofrio, Dallas, both of Tex.

[73] Assignee: Charles S. Martens, Los Angeles, Calif.

[21] Appl. No.: 688,458

[22] Filed: Apr. 22, 1991

[51] Int. Cl.$^5$ .............................................. A61K 7/043
[52] U.S. Cl. .......................................... 424/61; 424/59
[58] Field of Search ............................... 424/61; 524/40

[56] References Cited

U.S. PATENT DOCUMENTS

| | | | |
|---|---|---|---|
| 2,173,755 | 9/1939 | Fuller | 424/61 |
| 4,097,589 | 6/1978 | Shansky | 424/61 |
| 4,179,304 | 12/1979 | Rossomando | 424/61 |
| 4,229,227 | 10/1980 | Ikeda et al. | 106/181 |
| 4,301,046 | 11/1981 | Schlossman | 260/16 |
| 4,421,881 | 12/1983 | Benkendorf et al. | 524/24 |
| 4,649,045 | 3/1987 | Gaske et al. | 424/61 |
| 4,712,571 | 12/1987 | Remz et al. | 424/61 |
| 4,740,370 | 4/1988 | Faryniarz et al. | 424/61 |
| 4,747,419 | 5/1988 | Flynn et al. | 132/73 |
| 4,749,564 | 6/1988 | Faryniarz et al. | 424/61 |
| 4,798,720 | 1/1989 | Holder | 424/61 |
| 4,820,509 | 4/1989 | Yamazaki et al. | 424/61 |
| 4,897,261 | 1/1990 | Yamazaki et al. | 424/61 |

*Primary Examiner*—Thurman K. Page
*Assistant Examiner*—D. Colucci
*Attorney, Agent, or Firm*—Harris, Kern, Wallen & Tinsley

[57] ABSTRACT

A top coat composition for application over a nail polish, consisting essentially of cellulose acetate butyrate resin, a mixture of solvents for dissolving the cellulose acetate butyrate resin to form a first solution, a plasticizer for the first solution, and a solvent for the plasticizer, providing a dry non-tacky, non-brittle solid coat and which is quick drying when applied over a nail polish while wet with improved hardness and gloss.

8 Claims, No Drawings

NAIL POLISH TOP COAT

BACKGROUND OF THE INVENTION

This invention relates to nail polishes and more specifically, to a composition for applying over a nail polish. Such a composition is clear and is sometimes referred to as a "top coat", being applied over the color coat or coats.

For many years, nail polishes were applied as a single-color coat. In more recent times, nail polishes have been applied in layers, with different layers having different compositions and being used for different purposes.

One problem always present in the application of nail polishes is the length of time required for drying, especially where each layer must be dry before the next layer can be applied. Also, the final layer must be absolutely dry or it will be scratched or smeared when the wearer initiates another activity.

Accordingly, it is an important object of the present invention to provide a new nail polish top coat which can be applied over a wet layer of polish and which will dry in a very short time, typically, in less than one minute.

A prior composition for reducing the drying time is shown in the Holder U.S Pat. No. 4,798,720. The composition is a mixture of commercially available products, a top coat polish, an acrylic nail powder, an acrylic nail primer, and an adhesive. The top coat polish is a commercial product with a nitrocellulose base. In use, the new composition is applied as a base coat layer, a color polish is coated on top of the first layer, another layer of the new composition is applied over the color polish as the third layer, another coat of color polish is applied over the third layer, and another coat of the new composition is applied over the second color polish as the fifth layer.

Another prior composition is shown in the Shansky U.S Pat. No. 4,097,589. The composition of this patent utilizes a special copolyamide terpolymer to provide improved flexural strength.

However, none of these prior compositions provides the desired features of the ability to be applied over a wet nail polish and the exceedingly short drying time.

SUMMARY OF THE INVENTION

A top coat composition for application over a nail polish, incorporating cellulose acetate butyrate resin, a mixture of solvents for dissolving the cellulose acetate butyrate resin to form a first solution, a plasticizer for the first solution, a solvent for the plasticizer, the cellulose acetate butyrate resin and plasticizer being dissolved in the solvents, the plasticizer being present in an amount to provide a dry non-tacky, non-brittle solid coat and the cellulose acetate butyrate ester being present in an amount which is effective to provide quick drying of the composition when applied over a nail polish while wet with improved hardness and gloss.

Other options, advantages, features and results will more fully appear in the course of the following description.

DESCRIPTION OF THE PREFERRED EMBODIMENTS

The top coat composition is applied over a standard color nail polish while the polish is wet. The components of the composition are cellulose acetate butyrate ester (CAB), solvent for CAB, plasticizer, and solvent for the plasticizer. A ultraviolet bleaching material and a smoothing material may also be used.

The preferred constituents and sources for the constituents are set out in Table 1.

TABLE 1

| | Material | Supplier |
|---|---|---|
| 1. | toluene (CAB solvent) | generic |
| 2. | N-butyl acetate (CAB solvent) | generic |
| 3. | cellulose acetate butyrate ester 381 (CAB) | Eastman Chemical |
| 4. | cellulose acetate butyrate ester 551 (CAB) | Eastman Chemical |
| 5. | benzophenone-1 (UV block) | Neville-Synthese |
| 6. | butyl benzyl phthalate (plasticizer) | Monsanto Chemical |
| 7. | polysiloxane co-polymer (smoother) | BYK Chemical |
| 8. | isopropyl alcohol (solvent for 5,6 & 7) | generic |

The presently preferred embodiment of the top coat composition and the process of its manufacture are given in Example 1.

Example 1

| | | Quantity For One Gallon | % By Weight |
|---|---|---|---|
| 1. | toluene | 40.0 fl oz | 31.11 |
| 2. | N-butyl acetate | 48.0 fl oz | 38.00 |
| 3. | cellulose acetate butyrate ester 381 | 560 grams | 17.05 |
| 4. | cellulose acetate butyrate ester 551 | 80 grams | 2.44 |
| 5. | benzophenone-1 | 4 grams | 0.13 |
| 6. | butyl benzyl phthalate | 4.0 fl oz | 3.87 |
| 7. | polysiloxane co-polymer | 12 grams | 0.36 |
| 8. | isopropyl alcohol | 10.0 fl oz | 7.04 |

Charge solvents 1 and 2 into a high speed mixer. Add items 3 and 4 while running low speed. Run high speed 20 minutes until dissolved. Run low speed while adding items 5, 6, 7 and 8. Run low speed 20 minutes. Fill in containers.

This composition provides a protective coating for nail polish and dries quickly. The composition provides gloss, color, and light resistance to the nail polish, and adds a silky feel to nails.

Alternative embodiments are set out in Examples 2, 3 and 4.

Example 2

| | | Quantity For One Gallon | % By Weight |
|---|---|---|---|
| 1. | toluene | 40.0 fl oz | 31.11 |
| 2. | N-butyl acetate | 48.0 fl oz | 38.00 |
| 3. | cellulose acetate butyrate ester 381 | 640 grams | 19.49 |
| 5. | benzophenone-1 | 4 grams | 0.13 |
| 6. | butyl benzyl phthalate | 4.0 fl oz | 3.87 |
| 7. | polysiloxane co-polymer | 12 grams | 0.36 |
| 8. | isopropyl alcohol | 10.0 fl oz | 7.04 |

In Example 2 the composition is made with 100% CAB 381. However the mixture of CAB 381 and CAB 551 is preferred as it provides better sag resistance and easier application. The manufacturing process is the same as for Example 1.

| Example 3 | | |
|---|---|---|
| | Quantity For One Gallon | % By Weight |
| 1. Toluene | 40.0 fl oz | 31.11 |
| 2. N-butyl acetate | 48.0 fl oz | 38.00 |
| 3. Cellulose acetate butyrate ester 381 | 640 grams | 19.49 |
| 5. Benzophenone-1 | 4 grams | 0.13 |
| 6. Butyl benzyl phthalate | 4.0 fl oz | 3.87 |
| 8. Isopropyl alcohol | 10.0 fl oz | 7.40 |

In Example 3 the composition is made with 100% CAB 381 and 0% polysiloxane. The polysiloxane reduces surface friction and yields a silky feel. The manufacturing process is the same as for Examples 1 and 2.

| Example 4 | | |
|---|---|---|
| | Quantity For One Gallon | % By Weight |
| 1. toluene | 40.0 fl oz | 31.11 |
| 2. N-butyl acetate | 48.0 fl oz | 38.00 |
| 3. cellulose acetate butyrate ester 381 | 640 grams | 19.49 |
| 6. butyl benzyl phthalate | 4.0 fl oz | 3.87 |
| 8. isopropyl alcohol | 10.0 fl oz | 7.53 |

Benzophenone was used in the prior examples to give extra UV light protection. The manufacturing process is the same as for Examples 1, 2 and 3.

The top coat composition may be applied directly over a wet layer of nail polish, and dries in a very short time, typically in less than one minute, hardening as it cures. The finished coat has high resistance to chipping, flaking, peeling and bubbling. The resulting finish has high gloss and gloss retention and remains "wet looking", especially when the smoother material is utilized. As the top coat composition cures, it bonds to the underlying nail enamel forming a protective shield for the color layer or layers. The embodiment incorporating the ultra violet light blocking material inhibits the yellowing encountered with many nail polishes and permits longer wearing time.

I claim:

1. A clear top coat composition for application over a wet nail polish, consisting essentially of:
   cellulose acetate butyrate ester dissolved in a mixture of solvents consisting of toluene and n-butyl acetate, and
   a plasticizer butyl benzyl phthalate dissolved in isopropyl alcohol,
   said plasticizer being present in an amount to provide a dry non-tacky, non-brittle solid coat and said cellulose acetate butyrate ester being present in an amount which is effective to provide quick drying of the composition when applied over a nail polish while wet with improved hardness and gloss.

2. A composition as defined in claim 1 wherein said cellulose acetate butyrate ester is a mixture of cellulose acetate butyrate ester 381 and cellulose acetate butyrate ester 551.

3. A composition as defined in claim 1 including benzophenone-1 as an ultraviolet light blocking material.

4. A composition as defined in claim 3 including polysiloxane co-polymer as a smoothing material.

5. A clear and quick drying top coat composition for application over a wet nail polish, consisting essentially, in percent by weight, of about:
   toluene 31.11,
   N-butyl acetate 38.00,
   cellulose acetate butyrate ester 381 17.05,
   cellulose acetate butyrate ester 551 2.44,
   benzophenone-1 0.13,
   butyl benzyl phthalate 3.87,
   polysiloxane co-polymer 0.36,
   isopropyl alcohol 7.04.

6. A clear and quick drying top coat composition for application over a wet nail polish, consisting essentially, in percent by weight, of about:
   toluene 31.11,
   N-butyl acetate 38.00,
   cellulose acetate butyrate ester 381 19.49,
   benzophenone-1 0.13,
   butyl benzyl phthalate 3.87,
   polysiloxane co-polymer 0.36,
   isopropyl alcohol 7.04.

7. A clear and quick drying top coat composition for application over a wet nail polish, consisting essentially, in percent by weight, of about:
   toluene 31.11,
   N-butyl acetate 38.00,
   cellulose acetate butyrate ester 381 19.49,
   benzophenone-1 0.13,
   butyl benzyl phthalate 3.87.

8. A clear and quick drying top coat composition for application over a wet nail polish, consisting essentially, in percent by weight, of about:
   toluene 31.11,
   N-butyl acetate 38.00,
   cellulose acetate butyrate ester 381 19.49,
   butyl benzyl phthalate 3.87,
   isopropyl alcohol 7.53.

* * * * *